(12) United States Patent
Devic et al.

(10) Patent No.: US 8,946,493 B2
(45) Date of Patent: *Feb. 3, 2015

(54) METHOD FOR PRODUCING PENTAFLUOROPROPANE

(75) Inventors: Michel Devic, Sainte Foy les Lyon (FR); Nicolas Doucet, Lyons (FR); Laurent Wendlinger, Soucieu en Jarrest (FR); Geraldine Cavallini, Saint-Symphorien d'Ozon (FR)

(73) Assignee: Arkema France, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/377,189

(22) PCT Filed: May 6, 2010

(86) PCT No.: PCT/FR2010/050866
§ 371 (c)(1),
(2), (4) Date: Jan. 10, 2012

(87) PCT Pub. No.: WO2010/142878
PCT Pub. Date: Dec. 16, 2010

(65) Prior Publication Data
US 2012/0101315 A1   Apr. 26, 2012

(30) Foreign Application Priority Data
Jun. 12, 2009 (FR) ...................... 09 53937

(51) Int. Cl.
*C07C 17/354* (2006.01)
*C07C 19/08* (2006.01)

(52) U.S. Cl.
CPC .................................. *C07C 17/354* (2013.01)
USPC ......................................................... 570/175

(58) Field of Classification Search
CPC ...... C07C 17/354; C07C 19/08; C07C 21/18; C07C 17/00
USPC ................................................... 570/175, 124
See application file for complete search history.

(56) References Cited

U.S. PATENT DOCUMENTS

| 5,679,875 A | 10/1997 | Aoyama | |
| 2009/0131727 A1 * | 5/2009 | Yang et al. | 570/175 |

FOREIGN PATENT DOCUMENTS

| EP | 0644173 | 3/1995 |
| EP | 0726243 | 8/1996 |
| EP | 1916232 | 4/2008 |
| WO | WO 2008/030440 | 3/2008 |
| WO | WO 2009138764 A1 * | 11/2009 |

OTHER PUBLICATIONS

Knunyants, M.P., et al., Reactions of Fluoro Olefins, Journal of the USSR Academy of Sciences, Communications 13, Catalytic Hydrogeneration of Perfluoro Olefins, No. 8, Aug. 1960, pp. 1412-1418, Chem Abstracts acession No. 1961:2127.
Sianesi, D., et al., Fluoro Olefins I cis-and-trans-1-2-3-3-3-Pentafluoropropylene Ann. Chim (Rome), 55 (8-9), 1965, pp. 850-861, Chem Abstracts accession No. 1966:3555.

* cited by examiner

*Primary Examiner* — Jafar Parsa
*Assistant Examiner* — Medhanit Bahta
(74) *Attorney, Agent, or Firm* — Brinks Gilson & Lione

(57) ABSTRACT

The present invention relates to a method for producing 1,2,3,3,3-pentafluoropropane, involving reacting gaseous phase 1,2,3,3,3-pentafluoropropene with hydrogen in a superstoichimetric amount in the presence of a hydrogenation catalyst in a reactor, and recirculating a part of the gaseous effluent from the reactor.

12 Claims, No Drawings

METHOD FOR PRODUCING PENTAFLUOROPROPANE

FIELD OF THE INVENTION

The present invention relates to a process for the manufacture of 1,1,1,2,3-pentafluoropropane by hydrogenation of 1,2,3,3,3-pentafluoropropene.

BACKGROUND OF THE INVENTION 2,3,3,3-Tetrafluoropropene is known for its properties of refrigerant and heat-exchange fluid. The process for the manufacture of 2,3,3,3-tetrafluoropropene from 1,2,3,3,3-pentafluoropropene comprises a stage of hydrogenation of 1,2,3,3,3-pentafluoropropene.

The document by Knunyants et al., Journal of the USSR Academy of Sciences, Chemistry Department, "Reactions of fluoro-olefins", Report 13, "Catalytic hydrogenation of perfluoro-olefins", 1960, describes the hydrogenation of 1,2,3,3,3-pentafluoropropene (HFO-1225ye) at ambient temperature over a palladium catalyst supported on alumina to give a mixture of 1,1,1,2,3-pentafluoropropane (HFC-245eb) and 1,1,1,2-tetrafluoropropane (HFC-254eb). 1,1,1,2-Tetrafluoropropane is produced in a significant amount (that is to say, approximately 50% with respect to the 1,1,1,2,3-pentafluoropropane).

The document WO 2008/030440 describes a method for the preparation of 2,3,3,3-tetrafluoropropene comprising at least one hydrogenation stage during which 1,2,3,3,3-pentafluoropropene is brought into contact with hydrogen in the presence of a catalyst. According to this document, the hydrogenation catalyst which may be suitable comprises a metal from Group VIII or rhenium and the metal can be supported.

Example 1 of the document WO 2008/030440 describes the hydrogenation reaction of 1,2,3,3,3-pentafluoropropene at 85° C. in the presence of a catalyst comprising 0.5% by weight of palladium supported on charcoal to give a stream comprising 92% of HFC-245eb and 8% of HFC-254eb.

The tests of the abovementioned prior art were carried out on the laboratory scale and the documents are completely silent with regard to the lifetime of these catalysts.

The hydrogenation reactions as described above are highly exothermic reactions and present problems on the industrial scale. In addition, a not insignificant amount of byproduct (HFC-254eb) is formed, due probably to the successive hydrogenolysis reaction of the HFC-245eb (that is to say, the replacement of a fluorine atom of the desired product by a hydrogen atom with formation of hydrofluoric acid).
The presence of a compound other than the reactants in the reaction stream can also be the cause of a rapid deactivation of the catalyst.

Furthermore, the document EP 1 916 232 provides a multistage hydrogenation reaction of an olefinic compound in order to obtain a high conversion and a high selectivity. Example 2 describes the hydrogenation in stages of 1,2,3,3,3-pentafluoropropene in the presence of a palladium catalyst supported on charcoal in four reactors with an outlet temperature of the first reactor of 99° C., an outlet temperature of the second reactor of 95° C., for a conversion of 54%, a temperature at the outlet of the third reactor of 173° C. and a temperature at the outlet of the fourth reactor of 104° C. Provision is made for cooling stages between the reactors with a temperature of the first bath of 59° C. and a temperature of the second bath of 116° C.

The process as described in the document EP 1 916 232 is expensive and, in addition, it is not easy to carry out.

DETAILED DESCRIPTION OF THE INVENTION

The present patent application provides a continuous or semicontinuous process for the manufacture of 1,1,1,2,3-pentafluoropropane from 1,2,3,3,3-pentafluoropropene which makes it possible to solve, in all or in part, the abovementioned disadvantages.

The process according to the present invention makes it possible more particularly to control the exothermicity of the hydrogenation reaction and/or to limit the hydrogenolysis reaction of HFC-245eb and/or to reduce the deactivation of the catalyst.

The process according to the present invention is characterized in that (i) 1,2,3,3,3-pentafluoropropene is reacted in the gas phase with hydrogen in a superstoichiometric amount, at a temperature of between 80 and 250° C., preferably of between 110 and 160° C., in the presence of a hydrogenation catalyst in a reactor; (ii) a portion of the gaseous output stream resulting from the reactor, comprising 1,1,1,2,3-pentafluoropropane, unreacted hydrogen, optionally unreacted 1,2,3,3,3-pentafluoropropene, 1,1,1,2-tetrafluoropropane and hydrofluoric acid, is recycled and (iii) the 1,1,1,2,3-pentafluoropropane is recovered from the other portion of the output stream resulting from the reactor, optionally after a purification stage.

Preferably, the temperature at the inlet of the catalytic bed is between 50 and 200° C., advantageously between 80 and 140° C.

The stream recycled to the reactor and also the reactants can be preheated before introduction into the reactor.

The process according to the present invention is preferably carried out with a hydrogen/HFO-1225ye molar ratio of between 1.2 and 40, advantageously of between 3 and 10. This ratio is generally obtained by addition of 1,2,3,3,3-pentafluoropropene and hydrogen to the recycling stream.

The contact time, defined as the ratio of the volume of the catalytic bed to the flow rate by volume of the total stream under standard temperature and pressure conditions, is preferably between 0.1 and 20 s and advantageously between 0.5 and 5 s.

The hydrogenation reaction according to the present invention is preferably carried out at a pressure of between 0.5 and 20 bar absolute and advantageously of between 1 and 5 bar absolute.

The gaseous output stream at the outlet of the reactor preferably comprises from 5 to 96% by volume of the 1,1,1,2,3-pentafluoropropane, from 2 to 90% by volume of hydrogen, from 1 to 20% of 1,1,1,2-tetrafluoropropane and from 0 to 10% of the 1,2,3,3,3-pentafluoropropene.

Advantageously, the gaseous output stream at the outlet of the reactor comprises from 5 to 91% by volume of the 1,1,1,2,3-pentafluoropropane, from 8 to 50% by volume of hydrogen, from 1 to 5% by volume of 1,1,1,2-tetrafluoropropane and from 0 to 0.1% by volume of the 1,2,3,3,3-pentafluoropropene.

According to the process of the present invention, use is preferably made of an adiabatic reactor.

The portion of the gaseous output stream which is recycled to the reactor preferably represents at least 80% by volume of the whole of the output stream at the outlet of the reactor, advantageously at least 90% by volume. Particularly preferably, the portion of the output stream recycled to the reactor represents between 93 and 98% by volume of the total output stream at the outlet of the reactor.

Mention may in particular be made, as catalyst, of those based on a metal from Group VIII or rhenium. The catalyst can be supported, for example on carbon, alumina, aluminium fluoride, and the like, or can be unsupported, such as Raney nickel. Use may be made, as metal, of platinum or palladium, in particular palladium, advantageously supported on carbon or alumina. It is also possible to combine this metal with another metal, such as silver, copper, gold, tellurium, zinc, chromium, molybdenum and thallium.

The preferred catalyst comprises optionally supported palladium. The catalyst very particularly preferred according to the present invention is a catalyst comprising palladium on a support based on alumina. The amount of palladium in the catalyst is preferably between 0.05 and 10% by weight and advantageously between 0.1 and 5%.

The specific surface of the catalyst is preferably greater than 4 $m^2/g$. The alumina used as catalytic support is advantageously provided in the a polymorphic form.

The Applicant Company has noticed, surprisingly, that the amount of HFC-254eb byproduct remains low despite the recycling of a portion of the gaseous output stream at the outlet of the reactor. This amount is even lower in comparison with the prior art in the absence of recycling.

The process according to the present invention makes it possible to obtain a high conversion of the HFO-1225ye and a high selectivity for HFC-245eb. In addition, these performances are stable over time. This makes it possible to limit the presence of hydrofluoric acid (a highly corrosive product) in the recycling loop.

Experimental Part

The following tests were carried out with a device which makes it possible to recycle a portion of the output stream to the reactor.

The conversion is defined as being the percentage of HFO-1225ye which is converted.

The selectivity for product X is defined as being the percentage of the number of moles of product X formed with regard to the number of moles of HFO-1225ye converted.

Example 1

Use is made of a tubular reactor made of stainless steel, with an internal diameter of 2.1 cm and a length of 120 cm, containing 469 g, i.e. 320 $cm^3$, of catalyst in the form of a fixed bed. The catalyst comprises 0.2% by weight of palladium supported on α-alumina.

For the duration of the reaction, 1.41 mol/h of hydrogen and 0.7 mol/h of 1,2,3,3,3-pentafluoropropene are continuously injected and the flow rate of the recycling loop is 0.490 $Sm^3$, i.e. 93.7% by volume of the gaseous output stream at the outlet of the reactor. The hydrogen/HFO-1225ye molar ratio at the inlet of the catalytic bed is 16. The pressure is 1 bar absolute. The temperature at the inlet of the reactor is 60° C. and the maximum reactor temperature achieved during the reaction is 124° C. The contact time is 2.3 seconds, A conversion of HFO-1225ye of 100%, a selectivity for HFC-245eb of 95.7% and a selectivity for HFC-254eb of 4.1% are obtained.

No deactivation was observed during 80 h of operation.

Example 2

The same device as above is used with the same catalyst. For the duration of the reaction, 0.84 mol/h of hydrogen and 0.7 mol/h of 1,2,3,3,3-pentafluoropropene are continuously injected and the flow rate in the recycling loop is 0.970 $Sm^3/h$, i.e. a percentage of recycling by volume of 98%. The hydrogen/HFO-1225ye molar ratio at the inlet of the reactor is 1.18. The pressure is 2 bar absolute. The temperature at the inlet of the catalytic bed is 63° C. and the maximum reactor temperature achieved during the reaction is 90° C. The contact time is 1.2 S.

A conversion of HFO-1225ye of 100%, a selectivity for HFC-245eb of 79% and a selectivity for HFC-254eb of 20.0% are obtained.

Example 3

The operation is carried out under the same conditions as Example 2, except that the hydrogen/HFO-1225ye molar ratio at the inlet of the reactor is 5.2 and that the temperature at the inlet of the catalytic bed is 100° C. The maximum temperature achieved during the reaction is 123° C.

A conversion of HFC-1225ye of 100%, a selectivity for HFC-245eb of 89.6% and a selectivity for HFC-254eb of 10.2% are obtained.

The invention claimed is:

1. Process for the manufacture of 1,1,1,2,3-pentafluoropropane, comprising (i) reacting 1,2,3,3,3-pentafluoropropene in the gas phase with hydrogen in a superstoichiometric amount, at a temperature of between 80 and 250° C. in the presence of a hydrogenation catalyst in a reactor to produce a gaseous output stream, wherein the gaseous output stream comprises from 5 to 96% by volume of 1,1,1,2,3-pentafluoropropane, from 2 to 90% by volume of hydrogen, from 1 to 20% of 1,1,1,2-tetrafluoropropane and from 0 to 10% of 1,2,3,3,3-pentafluoropropene; (ii) recycling a first portion of the gaseous output stream from the reactor, comprising 1,1,1,2,3-pentafluoropropane, unreacted hydrogen, optionally unreacted 1,2,3,3,3-pentafluoropropene, 1,1,1,2-tetrafluoropropane and hydrofluoric acid, and (iii) recovering 1,1,1,2,3-pentafluoropropane from a second portion of the gaseous output stream from the reactor, optionally after a purification stage, wherein the recycled first portion of the gaseous output stream represents at least 80%, by volume of the output stream.

2. Process according to claim 1, characterized in that the catalyst comprises supported palladium.

3. Process according to claim 2, characterized in that the support is based on alumina.

4. Process according to claim 1, characterized in that the molar ratio of hydrogen to 1,2,3,3,3-pentafluoropropene is between 1.5 and 40.

5. Process according to claim 1, characterized in that the contact time in the reactor is between 0.2 and 20 s.

6. Process according to claim 1, characterized in that the reaction is carried out at a pressure of between 0.5 and 20 bar absolute.

7. Process according to claim 1, characterized in that it is carried out continuously.

8. Process according to claim 1, characterized in that the temperature is between 110 and 160° C.

9. Process according to claim 1, characterized in that between 93 and 98% by volume of the output stream is recycled.

10. Process according to claim 1, characterized in that the molar ratio of hydrogen to 1,2,3,3,3-pentafluoropropene is between 3 and 10.

11. Process according to claim 1, characterized in that the reaction is carried out at a pressure of between 1 and 5 bar absolute.

12. Process according to claim 1, characterized in that the contact time in the reactor is between 1 and 5 s.

\* \* \* \* \*